United States Patent
Reid et al.

(10) Patent No.: US 7,727,286 B2
(45) Date of Patent: Jun. 1, 2010

(54) STRETCH FABRICS WITH IMPROVED CHEMICAL RESISTANCE

(75) Inventors: Rona L. Reid, Houston, TX (US); Thoi H. Ho, Lake Jackson, TX (US); Selim Bensason, Houston, TX (US); Rajen M. Patel, Lake Jackson, TX (US); Antonio Batistini, Adliswil (CH)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 12/472,739

(22) Filed: Aug. 5, 2009

(65) Prior Publication Data

US 2010/0024134 A1 Feb. 4, 2010

Related U.S. Application Data

(60) Division of application No. 10/507,231, filed as application No. PCT/US2003/007592 on Mar. 11, 2003, now abandoned, which is a continuation-in-part of application No. 09/627,534, filed on Jul. 28, 2000, now Pat. No. 6,437,014.

(60) Provisional application No. 60/363,127, filed on Mar. 11, 2002.

(51) Int. Cl.
*D06L 3/08* (2006.01)
*D06L 3/00* (2006.01)

(52) U.S. Cl. .................. 8/108.1; 8/115.51; 8/115.6; 8/101; 8/107

(58) Field of Classification Search ............... 8/115.51, 8/115.6, 101, 107, 108.1
See application file for complete search history.

(56) References Cited

U.S. PATENT DOCUMENTS

| | | | |
|---|---|---|---|
| 3,097,192 A | 7/1963 | Schilit et al. |
| 3,333,024 A | 7/1967 | Haefele et al. |
| 3,396,529 A | 8/1968 | Stutz et al. |
| 3,507,609 A | 4/1970 | Gorrafa |
| 3,522,642 A | 8/1970 | Kunio et al. |
| 3,645,992 A | 2/1972 | Elston |
| 4,076,698 A | 2/1978 | Anderson et al. |
| 4,196,154 A | 4/1980 | Tung et al. |
| 4,200,718 A | 4/1980 | Tung et al. |
| 4,345,908 A | 8/1982 | Mohr, Jr. et al. |
| 4,798,081 A | 1/1989 | Hazlitt et al. |
| 5,008,204 A | 4/1991 | Stehling |
| 5,026,798 A | 6/1991 | Canich |
| 5,055,438 A | 10/1991 | Canich |
| 5,064,802 A | 11/1991 | Stevens et al. |
| 5,089,321 A | 2/1992 | Chum et al. |
| 5,108,820 A | 4/1992 | Kaneko et al. |
| 5,122,593 A | 6/1992 | Jennings et al. |
| 5,272,236 A | 12/1993 | Lai et al. |
| 5,278,272 A | 1/1994 | Lai et al. |
| 5,292,845 A | 3/1994 | Kawasaki et al. |
| 5,336,552 A | 8/1994 | Strack et al. |
| 5,350,423 A | 9/1994 | Davis, Jr. et al. |
| 5,352,744 A | 10/1994 | Bates et al. |
| 5,382,400 A | 1/1995 | Pike et al. |
| 5,529,830 A | 6/1996 | Dutta et al. |
| 5,612,422 A | 3/1997 | Hucul et al. |
| 5,645,253 A | 7/1997 | Hoshino |
| 5,665,800 A | 9/1997 | Lai et al. |
| 6,140,442 A | 10/2000 | Knight et al. |
| 6,194,532 B1 | 2/2001 | Maugans et al. |
| 6,248,355 B1 | 6/2001 | Seth |
| 6,337,313 B1 | 1/2002 | Rodrigues |
| 6,436,534 B1 | 8/2002 | Knight et al. |
| 6,437,014 B1 | 8/2002 | Ho et al. |
| 6,500,540 B1 | 12/2002 | Langohr et al. |
| 6,666,235 B2 | 12/2003 | Chi et al. |
| 2002/0081423 A1 | 6/2002 | Heffelfinger |

FOREIGN PATENT DOCUMENTS

| | | |
|---|---|---|
| EP | 0 416 815 A2 | 3/1991 |
| JP | 404185737 * | 6/1992 |
| WO | WO-99/63021 | 12/1999 |
| WO | WO-00/00229 A1 | 1/2000 |
| WO | WO-01/02630 A1 | 1/2001 |
| WO | WO-01/85843 | 11/2001 |

OTHER PUBLICATIONS

International Search Report (PCT/US03/07592).
Bates, Frank S., et al., Block Copolymers-Designer Soft Materials, Physics Today, Feb. 1999, pp. 32-38, vol. 52-Iss. 2, American Institute of Physics.
Tung, L.H., Block Copolymer Molecular Weight by GPC, Journal of Applied Polymer Science, 1979, pp. 953-963, vol. 24, John Wiley & Sons, Inc.

(Continued)

*Primary Examiner*—Lorna M Douyon
*Assistant Examiner*—Amina Khan

(57) ABSTRACT

Durable stretch fabrics are made and processed from one or more crosslinked, heat-resistant olefin elastic fibers, e.g., a substantially linear, homogeneously branched ethylene polymer. The fabrics can be made by any process, e.g., weaving, knitting, etc., and from any combination of crosslinked, heat-resistant olefin elastic and inelastic ("hard") fibers, e.g., cotton and wool. These fabrics exhibit excellent chemical, e.g., chlorine, resistance and durability, e.g., they retain their shape and feel ("hand") over repeated exposure to processing conditions, e.g., stone-washing, dye-stripping, PET-dyeing and the like, and service conditions, e.g., washing, drying, etc.

12 Claims, 5 Drawing Sheets

OTHER PUBLICATIONS

Falk, John C., Lithium Based Coordination Catalysts for the Hydrogenation of Diene and Vinylaromatic Polymers, Die Makromolekulare Chemie, 1972, pp. 291-299, vol. 160.

Santee, E.R., Jr. et al., 300 MHz Proton NMR of polybutadiene: Measurement of cis-trans Isomeric Content, Journal of Polymer Science: Polymer Letter Edition, 1973, pp. 449-452, vol. 11, John Wiley & Sons, Inc.

Wild, L. et al., Determination of Branching Distributions in Polyethylene and Ethylene Copolymers, Journal of Polymer Sciene: Polymer Physics Edition, 1982, pp. 441-455, vol. 20, John Wiley & Sons, Inc.

Randall, James C., A review of high resolution liquid 13Carbon Nuclear Magnetic Resonance Characterization of Ethylene-Based Polymers, Rev. Macromol. Chem. Phys. 1989, pp. 201-317, C29(2 &3).

Shida, M., et al., Correlation of Low Density Polyethylene Rheological Measurements with Optical and Processing Properties, Polymer Engineering and Science, 1977, pp. 769-774, vol. 17-No. 11.

Williams, T., et al., The construction of a polyethylene calibration curve for gel permeation chromatography using polystyrene fractions, Journal of Polymer Science: Polymer Letters, 1968, pp. 621-624, vol. 6.

"New Polyolefin Fiber Blend Makes Jeans WR and Quick-Drying." Daily News Record, April 1994.

Dealy, John M., Use of Compressed Gas to Drive Capillary Flow, Rheometers for molten plastics: a practical guide to testing and property measurement, 1982, pp. 97-100, Canadian Industries Limited, Montreal.

Hsieh, Henry, L., Block Copolymers, Anionic Polymerization: Principles and Practical Applications, 1996, pp. 307-331, Marcel Dekker, New York.

* cited by examiner

STRETCH FABRICS WITH IMPROVED CHEMICAL RESISTANCE

CROSS-REFERENCE TO RELATED APPLICATION

The present application is a divisional application of the U.S. application Ser. No. 10/507,231, filed on Sep. 9, 2004, entitled "STRETCH FABRIC WITH IMPROVED CHEMICAL RESISTANCE AND DURABILITY," the teachings of which are incorporated by reference herein, as if reproduced in full hereinbelow now abandoned, which is a 371 National Stage of International Application No. PCT/US2003/007592, filed on Mar. 11, 2003, entitled "STRETCH FABRIC WITH IMPROVED CHEMICAL RESISTANCE AND DURABILITY," the teachings of which are incorporated by reference herein, as if reproduced in full hereinbelow, and which claims priority from the U.S. Provisional Application No. 60/363,127, filed on Mar. 11, 2002, entitled "STRETCH FABRIC WITH IMPROVED CHEMICAL RESISTANCE AND DURABILITY," the teachings of which are incorporated by reference herein, as if reproduced in full hereinbelow. U.S. Provisional Application No. 60/363,127 is a continuation-in-part of U.S. Ser. No. 09/627,534 filed on Jul. 28, 2000 now U.S. Pat. No. 6,437,014.

BACKGROUND OF THE INVENTION

The present invention relates to stretch fabrics. In one aspect, the invention relates to stretch fabrics comprising synthetic and natural fibers while in another aspect, the invention relates to such fabrics comprising crosslinked, heat-resistant elastic fibers capable of withstanding dyeing and heat-setting processes. The crosslinked, heat-resistant elastic fibers are useful in various durable or repeated-use fabric applications such as, but not limited to, clothing, undergarments, sports apparel and upholstery. The crosslinked, heat-resistant elastic fibers can be conveniently formed into fabrics using well-known techniques such as, for example, by using co-knitting techniques with cotton, nylon, and/or polyester fibers.

A material is typically characterized as elastic if it has a high percent elastic recovery (that is, a low percent permanent set) after application of a biasing force. Ideally, elastic materials are characterized by a combination of three important properties, i.e., (i) a low percent permanent set, (ii) a low stress or load at strain, and (iii) a low percent stress or load relaxation. In other words, there should be (i) a low stress or load requirement to stretch the material, (ii) no or low relaxing of the stress or unloading once the material is stretched, and (iii) complete or high recovery to original dimensions after the stretching, biasing or straining is discontinued.

To be used in the durable fabrics, the fibers making up the fabric have to be, inter alia, stable during dyeing and heat setting processes. For an elastic polyolefin fiber to be stable under dyeing and heat-setting conditions, it must be crosslinked. These fibers can be crosslinked by one or more of a number of different methods, e.g., e-beam or UV irradiation, silane or azide treatment, peroxide, etc., some methods better than others for fibers of a particular composition. For example, polyolefin fibers that are irradiated under an inert atmosphere (as opposed to irradiated under air) tend to be highly stable during dyeing processes (that is, the fibers do not melt or fuse together). The addition of a mixture of hindered phenol and hindered amine stabilizers further stabilized such fibers at heat setting conditions (200-2100 C).

Lycra®, a segmented polyurethane elastic material manufactured by E. I. du Pont de Nemours Company, is currently used in various durable stretch fabrics. Lycra, however, is not stable at the typical high heat-setting temperatures (200-210° C.) used for polyethylene terephthalate (PET) fiber. Moreover, and similar to ordinary uncrosslinked polyolefin-based elastic materials, Lycra fabrics tend to lose their integrity, shape and elastic properties when subjected to elevated service temperatures such as those encountered in washing, drying and ironing. As such, Lycra can not be easily used in co-knitting applications with high temperature fibers such as polyester fibers.

SUMMARY OF THE INVENTION

According to this invention, a stone-washed fabricated article comprises a fabric that comprises a heat-resistant, crosslinked olefin elastic fiber and an inelastic fiber. In one embodiment, the fabric is a durable stretch fabric made and processed from one or more crosslinked, heat-resistant olefin elastic fibers. The fabrics can be made by any process, e.g., weaving, knitting, etc., and from any combination of crosslinked, heat-resistant olefin elastic and inelastic ("hard") fibers. These fabrics exhibit excellent chemical, e.g., chlorine, resistance and durability, e.g., they retain their shape and feel ("hand") over repeated exposure to service conditions, e.g., washing, drying, etc. For example, in one embodiment the fabric has a change in elasticity not in excess of about 10% and/or retains at least about 50% of its growth after exposure to a 5% by weight permanganate solution for a period of at least 90 minutes at a temperature of at least 140 F. In another embodiment, the fabric retains at least about 10% of its elasticity and/or at least about 50% of its growth after exposure to a 10% by weight hypochlorite solution for a period of at least 90 minutes at a temperature of at least 140 F.

The crosslinked, heat-resistant olefin elastic fibers include ethylene polymers, propylene polymers and fully hydrogenated styrene block copolymers (also known as catalytically modified polymers). The ethylene polymers include the homogeneously branched and the substantially linear homogeneously branched ethylene polymers as well as ethylene-styrene interpolymers. The other fibers of the fabric can vary widely, and they include virtually all know natural and synthetic fibers, particularly inelastic fibers. Typical of these other fibers are cotton, wool, silk, nylon, polyester, and the like. Usually the crosslinked, heat-resistant olefin elastic fibers comprise a minority of the fabric on a weight basis.

The fabrics of this invention include (i) a stone-washed elastic cotton fabric, (ii) a dye-stripped elastic nylon fabric, (iii) a brilliant-colored, dyed elastic polyester (e.g., PET) fabric, (iv) a dry-cleaned elastic fabric (e.g., a fabric that has been exposed to perchloroethylene), and (v) a chlorine- or bromine-exposed elastic fabric comprising one or more of polyester, nylon and cotton. All of these fabrics have been exposed to harsh and stringent processes that utilize chemicals and conditions that would degrade most conventional stretch fabrics because these chemicals and conditions would degrade the stretch fiber component of these fabrics. The fabrics of this invention, however, comprise a stretch fiber that is particularly resistant to such degradation and as such, the fabric containing these fibers exhibits surprising durability and chemical resistance.

BRIEF DESCRIPTION OF THE FIGURES

The FIG. 1 is a photograph of four heavy weight, denim fabric samples comprising fiber made from AFFINITY ethylene/1-octene copolymer. Each sample was subjected to a different stone wash protocol, i.e., the first (or top) sample to a vintage wash, the second to an antique wash, the third to a destructive wash, and the fourth (or bottom) sample to a bleach-out wash. The stretch properties of each sample after the washing protocol were essentially the same as the stretch properties before the washing protocol. The dark blue patch on top of the first or top sample is the color of each sample before it was stone washed.

DESCRIPTION OF THE PREFERRED EMBODIMENTS

Figure 1:
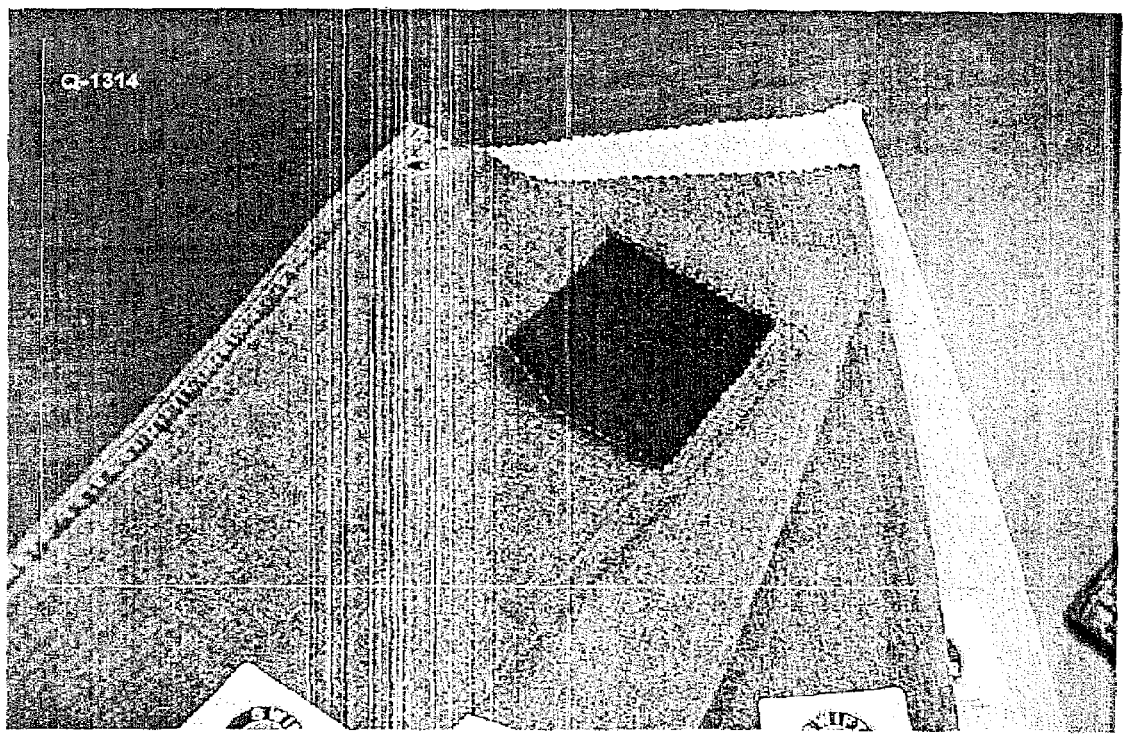

"Fiber" means a material in which the length to diameter ratio is greater than about 10. Fiber is typically classified according to its diameter. Filament fiber is generally defined as having an individual fiber diameter greater than about 15 denier, usually greater than about 30 denier. Fine denier fiber generally refers to a fiber having a diameter less than about 15 denier. Microdenier fiber is generally defined as fiber having a diameter less than about 100 microns denier.

"Filament fiber" or "monofilament fiber" means a single, continuous strand of material of indefinite (i.e., not predetermined) length, as opposed to a "staple fiber" which is a discontinuous strand of material of definite length (i.e., a strand which has been cut or otherwise divided into segments of a predetermined length).

The term "heat resistant" as used herein refers to the ability of an elastic polymer or elastic polymer composition in the form of fiber to pass the high temperature heat setting and dyeing tests described herein.

The term "elastic article" is used in reference to shaped items, while the term "elastic material" is a general reference to polymer, polymer blends, polymer compositions, articles, parts or items.

"Elastic" means that a fiber will recover at least about 50 percent of its stretched length after the first pull and after the fourth to 100% strain (doubled the length). Elasticity can also be described by the "permanent set" of the fiber. Permanent set is the converse of elasticity. A fiber is stretched to a certain point and subsequently released to the original position before stretch, and then stretched again. The point at which the fiber begins to pull a load is designated as the percent permanent set. "Elastic materials" are also referred to in the art as "elastomers" and "elastomeric". Elastic material (sometimes referred to as an elastic article) includes the polyolefin polymer itself as well as, but not limited to, the polyolefin polymer in the form of a fiber, film, strip, tape, ribbon, sheet, coating, molding and the like. The preferred elastic material is fiber. The elastic material can be either cured or uncured, radiated or unradiated, and/or crosslinked or uncrosslinked. For heat reversibility, the elastic fiber must be substantially crosslinked or cured.

"Nonelastic material" means a material, e.g., a fiber, that is not elastic as defined above.

"Meltblown fibers" are fibers formed by extruding a molten thermoplastic polymer composition through a plurality of fine, usually circular, die capillaries as molten threads or filaments into converging high velocity gas streams (e.g. air) which function to attenuate the threads or filaments to reduced diameters. The filaments or threads are carried by the high velocity gas streams and deposited on a collecting surface to form a web of randomly dispersed fibers with average diameters generally smaller than 10 microns.

The term "spunbond" is used herein in the conventional sense to refer to fibers formed by extruding the molten elastic polymer or elastic polymer composition as filaments through a plurality of fine, usually circular, die capillaries of a spinneret with the diameter of the extruded filaments then being rapidly reduced and thereafter depositing the filaments onto a collecting surface to form a web of randomly dispersed spunbond fibers with average diameters generally between 7 and 30 microns.

The term "nonwoven" as used herein and in the conventional sense means a web or fabric having a structure of individual fibers or threads which are randomly interlaid, but not in an identifiable manner as is the case for a knitted fabric. The elastic fiber of the present invention can be employed to prepare inventive nonwoven elastic fabrics as well as composite structures comprising the elastic nonwoven fabric in combination with nonelastic materials.

The term "conjugated" refers to fibers which have been formed from at least two polymers extruded from separate extruders but meltblown or spun together to form one fiber. Conjugated fibers are sometimes referred to in the art as multicomponent or bicomponent fibers. The polymers are usually different from each other although conjugated fibers may be monocomponent fibers. The polymers are arranged in substantially constantly positioned distinct zones across the cross-section of the conjugated fibers and extend continuously along the length of the conjugated fibers. The configuration of conjugated fibers can be, for example, a sheath/core arrangement (wherein one polymer is surrounded by another), a side by side arrangement, a pie arrangement or an "islands-in-the sea" arrangement. Conjugated fibers are described in U.S. Pat. Nos. 5,108,820, 5,336,552 and 5,382,400. The elastic fiber of the present invention can be in a conjugated configuration, for example, as a core or sheath, or both.

The term "thermal bonding" is used herein refers to the heating of fibers to effect the melting (or softening) and fusing of fibers such that a nonwoven fabric is produced. Thermal bonding includes calendar bonding and through-air bonding as well as methods known in the art. The expression "thermal bondable at a reduced hot melt adhesive amount" refers to comparative peel test results using Ato Findley Adhesive HX9275 (supplied by Ato Findley Nederlands B. V., Roosendaal, The Netherlands) or H. B. Fuller Adhesive D875BD1 (supplied by H. B. Fuller GmbH, IOneburg, Germany) and test procedures and methods described in WO 00/00229, wherein the same peel strength as the adhesive without deploying thermal bonding can be obtained even though the quantity of adhesive is at least 15 percent less where thermal bonding is deployed.

The term "polymer", as used herein, refers to a polymeric compound prepared by polymerizing one or more monomers. As used herein, generic term "polymer" embraces the terms "homopolymer," "copolymer," "terpolymer" as well as "interpolymer." A polymer is usually made in one reactor or polymerization vessel but can as well as be made using multiple reactors or polymerization vessels, although the latter is usually referred to as a polymer composition.

The term "polymer composition" as used herein refers to a mixture of a polymer and at least one ingredient added to or mixed with the polymer after the polymer is formed. Thus, the term "polymer composition" includes poly-blends (that is, admixtures of two or more polymers wherein each polymers is made in separate reactors or polymerization whether or not the reactors or vessels are part of the same polymerization system or not).

The term "interpolymer", as used herein refers to polymers prepared by the polymerization of at least two different types of monomers. As used herein the generic term "interpolymer" includes the term "copolymers" (which is usually employed to refer to polymers prepared from two different monomers) as well as the term "terpolymers" (which is usually employed to refer to polymers prepared from three different types of monomers).

"Radiated" or "irradiated" means that the elastic polymer or polymer composition or the shaped article comprised of the elastic polymer or elastic composition was subjected to at least 3 megarads (or the equivalent of 3 megarads) of radiation dosage whether or not it resulted in a measured decrease in percent xylene extractables (i.e., an increase in insoluble gel). Preferably, substantial crosslinking results from the irradiation. "Radiated" or "irradiated" may also refer to the use of UV-radiation at an appropriate dose level along with optional photoinitiators and photocrosslinkers to induce crosslinking.

The terms "crosslinked" and "substantially crosslinked" as used herein mean the elastic polymer or elastic polymer composition or the shaped article comprised of the elastic polymer or elastic polymer composition is characterized as having xylene extractables of less than or equal to 70 weight percent (that, is, greater than or equal to 30 weight percent gel content), preferably less than or equal to 40 weight percent (that is, greater than or equal to 60 weight percent gel content), more preferably less than or equal to 35 weight percent (that is; greater than or equal to 65 weight percent gel content), where xylene extractables (and gel content) are determined in accordance with ASTM D-2765.

The terms "cured" and "substantially cured" as used herein means the elastic polymer or elastic polymer composition or the shaped article comprised of the elastic polymer or elastic polymer composition was subjected or exposed to a treatment which induced crosslinking. As used herein, the terms also relate to the use of a grafted silane compound, e-beam and UV-radiation.

The terms "curable" and "crosslinkable" as used herein mean the elastic polymer or elastic polymer composition or the shaped article comprised of the elastic polymer or elastic polymer composition is not crosslinked and has not been subjected or exposed to treatment which induces crosslinking although the elastic polymer, elastic polymer composition or the shaped article comprised of the elastic polymer or elastic polymer composition comprises additive(s) or functionality that will effectuate crosslinking upon subjected or exposed to such treatment.

The term "pro-rad additive" as used herein means a compound which is not activated during normal fabrication or processing of the elastic polymer or elastic polymer composition, but can be activated by the application of temperatures (heat) substantially above normal fabrication or processing temperatures or ionizing energy (or both) (and especially with regard to article, part or item fabrication and processing) to effectuate some measurable gelation or preferably, substantial crosslinking.

In the practice of the present invention, curing, irradiation or crosslinking of the elastic polymers, elastic polymer compositions or articles comprising elastic polymers or elastic polymer compositions can be accomplished by any means known in the art, including, but not limited to, electron-beam irradiation, beta irradiation, X-rays, UV-radiation, controlled thermal heating, corona irradiation, peroxides, allyl compounds and gamma-radiation with or without crosslinking catalyst. Electron-beam and UV-radiation irradiation are the preferred technique for crosslinking the olefin polymer.

Preferably, the curing, irradiation, crosslinking or combination thereof provides a percent gel, as determined using xylene in accordance with ASTM D-2765, of greater than or equal to 30 weight percent, more preferably greater than or equal to 55 weight percent, most preferably greater than or equal to 60 weight percent. Suitable electron-beam irradiation equipment is available from Energy Services, Inc. Wilmington, Mass. with capabilities of at least 100 kilo-electron volts (KeV) and at least 5 kilowatts (Kw). Preferably, electrons are employed up to 70 megarads dosages. The irradiation source can be any electron beam generator operating in a range of 150 Kev to 12 mega-electron volts (MeV) with a power output capable of supplying the desired dosage. The electron voltage can be adjusted to appropriate levels which may be, for example, 100,000, 300,000, 1,000,000 or 2,000,000 or 3,000,000 or 6,000,000, or higher or lower. Many other apparati for irradiating polymeric materials are known in the art.

In the present invention, effective irradiation is usually carried out at a dosage between 3 megarads (Mrad) to megarads, preferably from 10 to 35 megarads, more preferably from 15 to 32 megarads, and most preferably from 19 to 28 megarads. Further, the irradiation can be conveniently carried out at room temperature. Preferably, irradiation is conducted while the article (or plurality of articles) is at lower temperatures throughout the exposure, such as, for example, at −50° C. to 40° C., especially at −20° C. to 30° C., more especially at 0° C. to 25° C., and most especially from 0° C. to 12° C. The irradiation can be carried out on-line (that is, during fabrication of the article), off-line (such as after fabrication of the article, for example, film, by unwinding or wrapping the fabricated article) or on-spool (as such in the case of fibers, and filaments). Preferably, the irradiation is carried out after shaping or fabrication of the article. Also, in a preferred embodiment, a pro-rad additive is incorporated into the elastic polymer or elastic polymer composition and the polymer or composition is subsequently irradiated with electron beam radiation at 8 to 32 megarads.

In another aspect of the invention, the irradiation is carried out under an inert or oxygen-limited atmosphere. Suitable atmospheres can be provided by the use of helium, argon, nitrogen, carbon dioxide, xenon and/or a vacuum. Substantial improvements in high temperature serviceability can be gained by using an inert or oxygen-limited atmosphere without any attendant substantial lost in elastic performance ordinarily associated with service or use at elevated temperatures.

Crosslinking can be promoted with a crosslinking catalyst, and any catalyst that will provide this function can be used. Suitable catalysts generally include organic bases, carboxylic acids, and organometallic compounds including organic titanates and complexes or carboxylates of lead, cobalt, iron, nickel, zinc and tin. Dibutyltindilaurate, dioctyltinmaleate, dibutyltindiacetate, dibutyltindioctoate, stannous acetate, stannous octoate, lead naphthenate, zinc caprylate, and cobalt naphthenate. Tin carboxylate, especially dibutyltindilaurate and dioctyltinmaleate, are particularly effective for this invention. The catalyst (or mixture of catalysts) is present in a catalytic amount, typically between 0.015 and 0.035 phr.

Representative pro-rad additives include, but are not limited to, azo compounds, organic peroxides and polyfunctional vinyl or allyl compounds such as, for example, triallyl cyanurate, triallyl isocyanurate, pentaerthritol tetramethacrylate, glutaraldehyde, ethylene glycol dimethacrylate, diallyl maleate, dipropargyl maleate, dipropargyl monoallyl cyanurate, dicumyl peroxide, di-tert-butyl peroxide, t-butyl perbenzoate, benzoyl peroxide, cumene hydroperoxide, t-butyl peroctoate, methyl ethyl ketone peroxide, 2,5-dimethyl-2,5-di(t-butyl peroxy)hexane, lauryl peroxide, tert-butyl peracetate, and azobisisobutyl nitrite and combination thereof. Preferred pro-rad additives for use in the present invention are compounds which have polyfunctional (that is, at least two) moieties such as C=C, C=N or C=O.

At least one pro-rad additive can be introduced to the ethylene interpolymer by any method known in the art. However, preferably the pro-rad additives) is introduced via a masterbatch concentrate comprising the same or different base resin as the ethylene interpolymer. Preferably, the pro-rad additive concentration for the masterbatch is relatively high for example, greater than or equal to 25 weight percent (based on the total weight of the concentrate).

The at least one pro-rad additive is introduced to the ethylene polymer in any effective amount. Preferably, the at least one pro-rad additive introduction amount is from 0.001 20 to 5 weight percent, more preferably from 0.005 to 2.5 weight percent and most preferably from 0.015 to 1 weight percent (based on the total weight of the substantially hydrogenated block polymer).

Suitable amine or nitrogen-containing stabilizers for use in the present invention include, but are not limited to, naphthylamines, for example, N-phenyl naphthylamines such as Naugard PAN supplied by Uniroyal); diphenylamine and derivatives thereof which are also referred to as secondary aromatic amines (for example, 4,4'-bis (oc, oc-dimethylbenzyl) diphenylamine which is supplied by Uniroyal Chemical under the designation Naugard® 445); p-phenylenediamines (for example, Wingstay 300 supplied by Goodyear); piperidines and derivatives thereof (for example, poly[[6-[(1,1, 3,3-tetramethylbutyl)amino]-1,3,5-triazine-2, 4-diyl][(2,2,6, 6-tetramethyl-4-piperidinyl)imino)-1, 6-hexanediyl[(2,2,6, 6-tetramethyl-4-piperidinyl)imino)]) which is supplied by Ciba Specialty Chemicals under the designation of Chimassorbe 944 as well as other substituted piperidines such as Chimassorb® 119, Tinuviri 622 and Tinuvin® 770, all three also supplied by Ciba Specialty Chemicals), and quinolines (for example, oxyquinolines and hydroquinolines such as polymeric 2,2,4-trimethyl-1,2-dihydroquinoline which is supplied by Vanderbilt Company under the designation Agerite® D).

Suitable amine or nitrogen-containing stabilizers also include the hybrid stabilizers such as aminophenols (for example, N,N'-hexamethylenebis-3-(3,5-di-tert-butyl-4-hydroxyphenyl)-propionamide), acylaminophenols (which are also referred to as 4-hydroyanilides) and the various hybrid stabilizers described in U.S. Pat. No. 5,122,593 that consist of a N-(substituted)-1-(piperazine-2-one alkyl) group at one end and a (3,5-dialkyl-4-hydroxyphenyl)-α,α-disubstituted acetamine at the other end.

Other suitable amine or nitrogen-containing stabilizers include carboxylic acid amides of aromatic mono and dicarboxylic acids and N-monosubstituted derivatives (e.g. N,N'-diphenylokamide and 2,2'-oxamidobisethyl-3-(3,5-di-tertbutyl-4-hydroxyphenyl)propionate which is supplied by Uniroyal Chemical under the designation Naugarde XL-1); hydrazides of aliphatic and aromatic mono- and dicarboxylic acids and N-acylated derivatives thereof; bis-acylated hydrazine derivatives; melamine; benzotriazoles, hydrazones; acylated derivatives of hydrazino-triazines; polyhydrazides; salicylaethylenediimines; salicylaloximes; derivatives of ethylenediamino tetraacetic acid; and aminotriazoles and acylated derivatives thereof.

Preferred amine or nitrogen-containing stabilizers for use in the present invention are diphenylamines, substituted piperidines and hydroquinolines. The most preferred amine or nitrogen-containing stabilizers are hindered amines since they tend to cause less detrimental polymer discoloration than aromatic amines.

Further, the at least one amine or nitrogen-containing stabilizer can be employed alone or in combination with one or more other stabilizer such as, for example, but not limited to, other amine or nitrogen-containing stabilizer; a hindered phenol (for example, 2,6-di-tert-butyl-4-methylphenol which is supplied by Koppers Chemical under the designation BHT; tetrakis(methylene 3-(3,5-di-tert-butyl-4-hydroxyphenyl) propionate) methane which is supplied by Ciba Specialty Chemicals under the designation Irganox 1010; Irganox 1076 supplied by Ciba Specialty Chemicals; Cyanox 1790 which is tris (4-t-butyl-3-hydroxy=2,6-dimethylbenzyl)-s-triazine-2, 4,6-(1H,3H,5H)-trione as supplied by Cytec; and Irganox 3114 which is 1,3,5-tris(3,5-di-tert-butyl-4-hydroxybenzyl)-1,3,5-triazinane-2,4,6-trione as supplied by Ciba Specialty Chemicals); a thioester (for example, dilauryl thiodipropionate which is supplied by Evans under the designation Evanstab® 12); a phosphite (for example, Irgafos® 168 supplied by Ciba Specialty Chemicals and tri(nonylphenyl) phosphite which is supplied by Uniroyal Chemical under the designation Naugard® P); diphosphite (for example, distearyl pentaerthritol diphosphite which is supplied by Borg-Warner under the designation Westori 618); a. polymeric phosphite (for example, Wytox .345-S(1) supplied by Olin); phosphited phenol and bisphenol (for example, WytoX 604 supplied by Olin); and diphosphonite (for example, tetrakis(2,4-di-tert-butylphenyl) 4,4'-biphenylylene diphosphonite which is supplied by Sandos under the designation Sandostab® P-EPQ). A preferred combination is a hindered amine and a hindered phenol. With regard to hindered phenols, Cyanox 1790 and Irganox 3114 are preferred since these stabilizers tend to have a less detrimental effect on discoloration (due to nitroxide gas formation) than Irganox 1076 or Irganox 1010.

Preferably, the at least one amine or nitrogen-containing stabilizer (and optional other stabilizer) is added to the homogeneously branched ethylene polymer or the substantially hydrogenated block polymer or both in a melt compounding step, more preferably by the use of an additive concentrate, prior to fabrication and shaping process steps. The at least one nitrogen-containing stabilizer (and the optional other stabilizer) can be added to the interpolymer or block polymer at any effective concentration. But, preferably, the total stabilizer concentration is in the range of from 0.02 to 2 weight percent (based on the total weight of the stabilizer and interpolymer and/or block polymer), more preferably in the range from 0.075 to 1 weight percent (based on the total weight of the stabilizer and the interpolymer and/or block polymer) and most preferably in the range of from 0.1 to 0.32 weight percent (based on the total weight of the stabilizer and the interpolymer and/or block). Where an optional other stabilizer is used (for example, a hindered phenol), the concentration of the amine to the phenol is in-the range from 2:1 to 1:2, preferably in the range of from 1.25:1 to 1:1.25.

An especially preferred embodiment is a combination of amine with a phenol and a phosphorus-containing stabilizer, more preferably where the total concentration of the phenol and a phosphorus-containing stabilizer is less than or equal to 0.15 weight percent and the amine or nitrogen-containing stabilizer concentration is in the range of 0.15 to 0.32 weight percent.

In-process additives, for example, calcium stearate, water, and fluoropolymers, may-also be used for purposes such as for the deactivation of residual catalyst or improved processability or both. Colorants, coupling agents and fire retardants may also be include as longer as their incorporation does not disturb the desirable characteristics of the invention.

Suitable polymers for use in the present invention include ethylene-α-olefin interpolymers, substantially hydrogenated block polymers, styrene butadiene styrene block polymers, styrene-ethylenelbutene-styrene block polymers, ethylene styrene interpolymers, polypropylenes, polyamides, polyurethanes and any combination thereof. The preferred polymers are homogeneously branched ethylene-α olefin interpolymers.

The term "substantially hydrogenated block polymer" as used herein means a block copolymer that is characterized as having a hydrogenation level of greater than 90 percent (by number) for each vinyl aromatic monomer unit block and a hydrogenation level of greater than 95 percent (by number) for each conjugated diene polymer block, where for both the vinyl aromatic monomer and conjugated diene monomer repeating unit blocks, hydrogenation converts unsaturated moieties into saturated moieties. These polymers are more fully described in U.S. Ser. No. 09/627,534 filed on Jul. 28, 2000.

The term "partially hydrogenated block polymer" as used herein means a block polymer that is hydrogenated but does not meet the hydrogenation levels that define a substantially hydrogenated block polymer.

Substantially hydrogenated block copolymers comprise at least one distinct block of a hydrogenated polymerized vinyl aromatic monomer and at least one block of a hydrogenated polymerized conjugated diene monomer. Preferred substantially hydrogenated block polymers are triblock comprising (before hydrogenation) two vinyl aromatic monomer unit blocks and one conjugated diene monomer unit block. Suitable substantially hydrogenated block polymers for use in the present invention are generally characterized by:

a) a weight ratio of conjugated diene monomer unit block to vinyl aromatic monomer unit block before hydrogenation of greater than 60:40 b) a weight average molecular weight (MW) before hydrogenation of from 30,000 to 150,000 (preferably, especially for high drawdown application such as, for example, fiber spinning, less than or equal to 81,000), wherein each vinyl aromatic monomer unit block (A) has a weight average molecular weight, Mwa, of from 5,000 to 45,000 and each conjugated diene monomer unit block (B) has a weight average molecular weight, Mwb, of from 12,000 to 110,000; and c) a hydrogenation level such that each vinyl aromatic monomer unit block is hydrogenated to a level of greater than 90 percent and each conjugated diene monomer unit block is hydrogenated to a level of greater than 95 percent, as determined using UV-VIS spectrophotometry and proton NMR analysis.

Neat substantially hydrogenated block polymers can be further characterized as having a viscosity at 0.1 rad/sec and 190° C., as determined using a parallel plate rheometer (Rheometrics RMS-800 equipped with 25 mm diameter flat plates at 1.5 mm gap under a nitrogen purge), that is less than 1,000,000 poises, preferably less than or equal to 750,000 poises, more preferably less than 500,000 poises or that is at least 30 percent, preferably at least 50 percent, more preferably at least 80 lower than that of a partially hydrogenated block polymer having the same monomer types, number of monomer units, symmetry and weight average molecular weight, or that is defined by the following inequality:

Ln viscosity at 0.1 rad/sec #(7.08×10−5)(*MW*)+7.89 where "Ln" means natural log, and "#" means less than or equal to.

Neat substantially hydrogenated block polymers can also be further characterized as having a drawability of less than or equal to 200 denier, preferably less than or equal to 175 denier, more preferably less than or equal to 50 denier when fiber spun at 0.43 g/minute and 250° C. using an Instron capillary rheometer equipped with a die having a 1,000 micron diameter and a 20:1 L/D. The term "neat" is used herein to mean unblended with other synthetic polymer.

The vinyl aromatic monomer is typically a monomer of the formula:

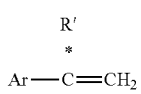

wherein R' is hydrogen or alkyl, Ar is phenyl, halophenyl, alkylphenyl, alkylhalophenyl, naphthyl, pyridinyl, or anthracenyl, wherein any alkyl group contains 1 to 6 carbon atoms which may be mono or multisubstituted with functional groups such as halo, nitro, amino, hydroxy, cyano, carbonyl and carboxyl. More preferably Ar is phenyl or alkyl phenyl with phenyl being most preferred. Typical vinyl aromatic monomers include styrene, alpha-methylstyrene, all isomers of vinyl toluene, especially para-vinyl toluene, all isomers of ethyl styrene, propyl styrene, butyl styrene, vinyl biphenyl, vinyl naphthalene, vinyl anthracene and mixtures thereof. The block copolymer can contain more than one specific polymerized vinyl aromatic monomer. In other words, the block copolymer can contain a polystyrene block and a poly-α-methylstyrene block. The hydrogenated vinyl aromatic block may also be a copolymer, wherein the hydrogenated vinyl aromatic portion is at least 50 weight percent of the copolymer.

The conjugated diene monomer can be any monomer having 2 conjugated double bonds. Such monomers include for example 1,3-butadiene, 2-methyl-1,3-butadiene, 2-methyl-1, 3-pentadiene, isoprene and similar compounds, and mixtures thereof. The block copolymer can contain more than one specific polymerized conjugated diene monomer. In other words, the block copolymer can contain a polybutadiene block and a polyisoprene block.

The conjugated diene polymer block can comprise materials that remain amorphous after the hydrogenation process, or materials which are capable of crystallization after hydrogenation. Hydrogenated polyisoprene blocks remain amorphous, while hydrogenated polybutadiene blocks can be either amorphous or crystallizable depending upon their structure. Polybutadiene can contain either a 1,2 configuration, which hydrogenates to give the equivalent of a 1-butene repeat unit, or a 1,4-configuration, which hydrogenates to give the equivalent of an ethylene repeat unit. Polybutadiene blocks having at least approximately 40 weight percent 1,2-butadiene content, based on the weight of the polybutadiene block, provides substantially amorphous blocks with low glass transition temperatures upon hydrogenation. Polybutadiene blocks having less than approximately 40 weight percent 1,2-butadiene content, based on the weight of the polybutadiene block, provide crystalline blocks upon hydrogenation. Depending on the final application of the polymer it may be desirable to incorporate a crystalline block (to improve solvent resistance) or an amorphous, more compliant block. In some applications, the block copolymer can contain more than one conjugated diene polymer block, such as a polybutadiene block and a polyisoprene block. The conjugated diene polymer block may also be a copolymer of a conjugated diene, wherein the conjugated diene portion of the copolymer is at least 50 weight percent of the copolymer. The conjugated diene polymer block may also be a copolymer of more than one conjugated diene, such as a copolymer of butadiene and isoprene. Also, other polymeric blocks may also be included in the substantially hydrogenated block polymers used in the present invention.

A "block" is herein defined as a polymeric segment of a copolymer which exhibits microphase separation from a structurally or compositionally different polymeric segment of the copolymer. Microphase separation occurs due to the incompatibility of the polymeric segments within the block copolymer. The separation of block segments can be detected by the presence of distinct glass transition temperatures. Microphase separation and block copolymers are generally discussed in "Block Copolymers-Designer Soft Materials", PHYSICS TODAY, February, 1999, pages 32-38. Suitable substantially hydrogenated block polymers typically have a weight ratio of conjugated diene monomer unit block to vinyl aromatic monomer unit block before hydrogenation of from 60:40 to 95:5, preferably from 65:35 to 90:10, more preferably from 70:30 to 85:15, based on the total weight of the conjugated diene monomer unit and vinyl aromatic monomer unit blocks.

The total weights of the vinyl aromatic monomer unit block(s) and the conjugated diene monomer unit block(s) before hydrogenation is typically at least 80 weight percent, preferably at least 90, and more preferably at least 95 weight percent of the total weight of the hydrogenated block polymer. More specifically, the hydrogenated block polymer typically contains from 1 to 99 weight percent of a hydrogenated vinyl aromatic polymer (for example, polyvinylcyclohexane or PVCH block, generally from 10, preferably from 15, more preferably from 20, even more preferably from 25, and most preferably from 30 to 90 weight percent, preferably to 85 and most preferably to 80 percent, based on the total weight of the hydrogenated block polymer. And, as to the conjugated diene polymer block, the hydrogenated block copolymer typically contains from 1 to 99 weight percent of a hydrogenated conjugated diene polymer block, preferably from 10, more preferably from 15, and most preferably from 20 to 90 weight percent, typically to 85, preferably to 80, more preferably to 75, even more preferably to 70 and most preferably to 65 percent, based on the total weight of the copolymer.

The substantially hydrogenated block polymers suitable for use in the present invention are produced by the hydrogenation of block copolymers including triblock, multiblock, tapered block, and star block polymers such as, for example, but not limited to, SBS, SBSBS, SIS, SISIS, and SISBS (wherein S is polystyrene, B is polybutadiene and I is polyisoprene). Preferred block polymers contain at least one block segment comprised of a vinyl aromatic polymer block, more preferably the block polymer is symmetrical such as, for example, a triblock with a vinyl aromatic polymer block on each end. The block polymers may, however, contain any number of additional blocks, wherein these blocks may be attached at any point to the triblock polymer backbone. Thus, linear blocks would include, for example, SBS, SBSB, SBSBS, and SBSBSB. That is, suitable block polymers include asymmetrical block polymers and tapered linear block polymers. The block polymer can also be branched, wherein polymer chains are attached at any point along the polymer backbone. In addition, blends of any of the aforementioned block copolymers can also be used as well as blends of the block copolymers with their hydrogenated homopolymer counterparts. In other words, a hydrogenated SBS block polymer can be blended with a hydrogenated SBSBS block polymer or a hydrogenated polystyrene homopolymer or both. It should be noted here that in the production of triblock polymers, small amounts of residual diblock copolymers are often produced.

The weight average molecular weight (MW) of suitable substantially hydrogenated block polymers, as measured before hydrogenation, is generally from 30,000, preferably from 45,000, more preferably from 55,000 and most preferably from 60,000 to 150,000, typically to 140,000, generally to 135,000, preferably to 130,000, more preferably to 125,000, and most preferably to 120,000. But preferably, especially when used neat (that is, without being blended with other polymer) for fiber melt spinning purposes, the weight average molecular weight before hydrogenation will be less than or 20 equal to 81,500, more preferably less than or equal to 75,000 and most preferably less than or equal to 67,500. Substantially hydrogenated block polymers can have vinyl aromatic monomer unit block with weight average molecular weights, Mw, before hydrogenation of from 6,000, especially from 9,000, more-especially from 11,000, and most especially from 12,000 to 45,000, especially to 35,000, more especially to 25,000 and most especially to 20,000. The weight average molecular weight of the conjugated diene monomer unit block before hydrogenation can be from 12,000, especially from 27,000, more especially from 33,000 and most especially from 36,000 to 110,000, especially to 100,000, more especially to 90,000 and most especially to 80,000. But preferably, especially when used neat for fiber melt spinning purposes, for triblocks comprising two hydrogenated vinyl aromatic monomer unit blocks and one hydrogenated conjugated diene monomer unit block, the weight average molecular weight of each vinyl aromatic monomer unit block before hydrogenation will be less than or equal to 15,000, more preferably less than or equal to 13,000 and most preferably less than or equal to 12,000.

It is important to note that each individual block of the hydrogenated block copolymer of the present invention, can have its own distinct molecular weight. In other words, for example, two vinyl aromatic polymer blocks may each have a different molecular weight. Mp and MW, as used to throughout the specification, are determined using gel permeation chromatography (GPC). The molecular weight of the substantially hydrogenated block polymer and properties obtained are dependent upon the molecular weight of each of the monomer unit blocks. For substantially hydrogenated block polymers, molecular weights are determined by comparison to narrow polydispersity homopolymer standards corresponding to the different monomer unit segments (for example, polystyrene and polybutadiene standards are used for SBS block copolymers) with adjustments based on the composition of the block copolymer. Also for example, for a triblock copolymer composed of styrene (S) and butadiene (B), the copolymer molecular weight can be obtained by the following equation:

$$lnMc = xlnMa + (1-x)lnMb$$

where Mc is the molecular weight of the copolymer, x is the weight fraction of S in the copolymer, Ma is the apparent molecular based on the calibration for S homopolymer and Mb is the apparent molecular weight based on the calibration for homopolymer B. This method is described in detail by L. H. Tung, Journal of Applied Polymer Science, volume 24, 953, 1979.

Methods of making block polymers are well known in the art. Typically, block polymers are made by anionic polymerization, examples of which are cited in Anionic Polymerization Principles and Practical Applications, H. L. Hsieh and R. P. Quirk, Marcel Dekker, New York, 1996. Block polymers can be made by sequential monomer addition to a carbanionic initiator such as sec-butyl lithium or n-butyl lithium. Block polymers can also be made by coupling a triblock material with a divalent coupling agent such as 1,2-dibromoethane, dichlorodimethylsilane, or phenylbenzoate. In this method, a small chain (less than 10 monomer repeat units) of a conjugated diene monomer can be reacted with the vinyl aromatic monomer unit coupling end to facilitate the coupling reaction. Note, however, vinyl aromatic polymer blocks are typically difficult to couple, therefore, this technique is commonly used to achieve coupling of the vinyl aromatic polymer ends. The small chain of the conjugated diene monomer unit does not constitute a distinct block since no microphase separation is achieved.

Coupling reagents and strategies which have been demonstrated for a variety of anionic polymerizations are discussed in Hsieh and Quirk, Chapter 12, pgs. 307-331. In another method, a difunctional anionic initiator is used to initiate the polymerization from the center of the block system, wherein subsequent monomer additions add equally to both ends of the growing polymer chain. An example of a such a difunctional initiator is 1,3-bis(1-phenylethenyl) benzene treated with organolithium compounds, as described in U.S. Pat. Nos. 4,200,718 and 4,196,154.

After preparation of the block polymer, the polymer is hydrogenated to remove sites of unsaturation in both the conjugated diene monomer unit block(s) and the vinyl aromatic monomer unit block(s) of the polymer. Any method of hydrogenation can be used where suitable methods typically include the use of metal catalysts supported on an inorganic substrate, such as Pd on $BaSO_4$ (U.S. Pat. No. 5,352,744) and Ni on kieselguhr (U.S. Pat. No. 3,333,024). Additionally, soluble, homogeneous catalysts such those prepared from combinations of transition metal salts of 2-ethylhexanoic acid and alkyl lithiums can be used to fully saturate block copolymers, as described in Die Makromolekulare Chemie, Volume 160, pp. 291, 1972. Hydrogenation can also be achieved using hydrogen and a heterogeneous catalyst such as those described in U.S. Pat. Nos. 5,352,744; 5,612,422 and 5,645,253. The catalysts described therein are heterogeneous catalysts consisting of a metal crystallite supported on a porous silica substrate. An example of a silica supported catalyst which is especially useful in the polymer hydrogenation is a silica which has a surface area of at least 10 $m^2/g$ which is synthesized such that it contains pores with diameters ranging between 3000 and 6000 angstroms. This silica is then impregnated with a metal capable of catalyzing hydrogenation of the polymer, such as nickel, cobalt, rhodium, ruthenium, palladium, platinum, other Group VIII metals, combinations or alloys thereof. Other heterogeneous catalysts can also be used, having average pore diameters in the range of 500 to 3,000 angstroms.

The level of hydrogenation of the substantially hydrogenated block polymers used in the present invention is greater than 95 percent for the conjugated diene monomer unit block(s) and greater than 90 percent for the vinyl aromatic monomer unit block(s), preferably greater than 99 percent for the conjugated diene monomer unit block(s) and greater than 95 percent for the vinyl aromatic monomer unit block(s), more preferably greater than 99.5 percent for the conjugated diene monomer unit block(s) and greater than 98 percent for the vinyl aromatic monomer unit block(s), and most preferably greater than 99.9 percent for the conjugated diene monomer unit block(s) and 99.5 percent for the vinyl aromatic monomer unit block(s).

The term "level of hydrogenation" refers to the percentage of the original unsaturated bonds that become saturated upon hydrogenation. The level of hydrogenation for the (hydrogenated) vinyl aromatic monomer unit block(s) can be determined using gamma-VIS spectrophotometry, while the level of hydrogenation for the (hydrogenated) diene conjugated monomer unit block(s) can be determined using proton NMR. The block polymer composition (that is, ratio of conjugated diene monomer unit blocks to vinyl aromatic monomer unit blocks) can be determined using proton NMR and a comparative integration technique such as that described by Santee, Chang and Morton in Journal of Polymer Science: Polymer Letter Edition, Vol. 11, page 449 (1973). Conveniently, a Varian Inova NMR unit set at 300 MHz for 1 H is used and samples of the block polymer are analyzed as 4 percent solutions (w/v) in CDC13 (deuterochloroform). Individual block lengths can be calculated from the weight average molecular weight, Mw, and 1 H NMR compositional analysis and by assuming a symmetrical structure (for example, a triblock with terminal polystyrene blocks).

The term "homogeneously branched ethylene polymer" is used herein in the conventional sense to refer to an ethylene interpolymer in which the comonomer is randomly distributed within a given polymer molecule and wherein substantially all of the polymer molecules have the same ethylene to comonomer molar ratio. The term refers to an ethylene interpolymer that are manufactured using so-called homogeneous or single-site catalyst systems known in the art such Ziegler vanadium, hafnium and zirconium catalyst systems and metallocene catalyst systems for example, a constrained geometry catalyst systems which is further described herein below.

Homogeneously branched ethylene polymers for use in the present invention can be also described as having less than 15 weight percent, preferably less 10 weight percent, more preferably less than 5 and most preferably zero (0) weight percent of the polymer with a degree of short chain branching less than or equal to 10 methyls/1000 carbons. That is, the polymer contains no measurable high density polymer fraction (for example, there is no fraction having a density of equal to or greater than 0.94 g/cm3), as determined, for example, using a temperature rising elution fractionation (TREF) technique and infrared or 13 C nuclear magnetic resonance (NMR) analysis.

Preferably, the homogeneously branched ethylene polymer is characterized as having a narrow, essentially single melting TREF profile/curve and essentially lacking a measurable high density polymer portion, as determined using a temperature rising elution fractionation technique (abbreviated herein as "TREF"). The composition distribution of an ethylene interpolymer can be readily determined from TREE as described, for example, by Wild et al., Journal of Polymer Science, Poly. Phys. Ed., Vol. 20, p. 441 (1982), or in U.S. Pat. Nos. 4,798,081 and 5,008,204; or by L. D. Cady, "The Role of Comonomer Type and Distribution in LLDPE Product Performance," SPE Regional Technical Conference, Quaker Square Hilton, Akron, Ohio, October 1-2, pp. 107-119 (1985).

The composition (monomer) distribution of the interpolymer can also be determined using 13 C NMR analysis in accordance with techniques described in U.S. Pat. No. 5,292,845; U.S. Pat. No. 4,798,081; U.S. Pat. No. 5,089,321 and by J. C. Randall, Rev. Macromol. Chem. Phys., C29, pp. 201-317 (1989). In analytical temperature rising elution fractionation analysis (as described in U.S. Pat. No. 4,798,081 and abbreviated herein as "ATREF"), the polymer, polymer composition or article to be analyzed is dissolved in a suitable hot solvent (for example, trichlorobenzene) and allowed to crystallized in a column containing an inert support (stainless steel shot) by slowly reducing the temperature. The column is equipped with both a refractive index detector and a differential viscometer (DV) detector. An ATREF-DV chromatogram curve is then generated by eluting the crystallized polymer sample from the column by slowly increasing the temperature of the eluting solvent (trichlorobenzene). The ATREF curve is also frequently called the short chain branching distribution (SCBD) or composition distribution (CD) curve, since it indicates how evenly the comonomer (for example, 1-octene) is distributed throughout the sample in that as elution temperature decreases, comonomer content increases. The refractive index detector provides the short chain distribution information and the differential viscometer detector provides an estimate of the viscosity average molecular weight. The composition distribution and other compositional information can also be determined using crystallization analysis fractionation such as the CRYSTAF fractionalysis package available commercially from PolymerChar, Valencia, Spain.

Preferred homogeneously branched ethylene polymers (such as, but not limited to, substantially linear ethylene polymers) have a single melting peak between −30 and 150° C., as determined using differential scanning calorimetry (DSC), as opposed to traditional Ziegler polymerized heterogeneously branched ethylene polymers (for example, LLDPE and ULDPE or VLDPE) which have two or more melting points. The single melting peak is determined using a differential scanning calorimeter standardized with indium and deionized water. The method involves about 5-7 mg sample sizes, a "first heat" to about 180° C. which is held for 4 minutes, a cool down at 10° C./min. to −30° C. which is held for 3 minutes, and heat up at 10° C./min. to 150° C. to provide a "second heat" heat flow vs. temperature curve from which the melting peak(s) is obtained. Total heat of fusion of the polymer is calculated from the area under the curve.

The at least one homogeneously branched ethylene interpolymer to be irradiated and/or crosslinked has a density at 23° C. less than 0.90 g/cm$^3$, preferably less than or equal to 0.88 g/cm$^3$, more preferably less than or equal to 0.87 g/cm$^3$, and especially in the range of 0.86 g/cm$^3$ to 0.875 g/cm$^3$, as measured in accordance with ASTM D792. Preferably, the homogeneously branched ethylene interpolymer is characterized as having a melt index less than 100 g/10 minutes, more preferably less than 30, most preferably less than 10 g/10 minutes or in the range of 3 to 12 g/10 minutes, as determined in accordance with ASTM D-1238, Condition 190° C./2.16 kilogram (kg). ASTM D-1238, Condition 190° C./2.16 kilogram (kg) are referred to herein as I$_2$ melt index.

The homogeneously branched ethylene polymers for use in the invention can be either a substantially linear ethylene polymer or a homogeneously branched linear ethylene polymer. The term "linear" as used herein means that the ethylene polymer does not have long chain branching. That is, the polymer chains comprising the bulk linear ethylene polymer have an absence of long chain branching, as in the case of traditional linear low density polyethylene polymers or linear high density polyethylene polymers made using Ziegler polymerization processes (for example, U.S. Pat. No. 4,076,698), sometimes called heterogeneous polymers. The term "linear" does not refer to bulk high pressure branched polyethylene, ethylene/vinyl acetate copolymers, or ethylene/vinyl alcohol copolymers which are known to those skilled in the art to have numerous long chain branches.

The term "homogeneously branched linear ethylene polymer" refers to polymers having a narrow short chain branching distribution and an absence of long chain branching. Such "linear" uniformly branched or homogeneous polymers include those made as described, for example, in U.S. Pat. No. 3,645,992 and those made, for example, using so called single site catalysts in a batch reactor having relatively high ethylene concentrations (as described in U.S. Pat. Nos. 5,026,798 or 5,055,438) or those made using vanadium catalysts or those made using constrained geometry catalysts in a batch reactor also having relatively high olefin concentrations (as described in U.S. Pat. No. 5,064,802 or in EP 0 416 815 A2).

Typically, homogeneously branched linear ethylene polymers are ethylene/α-olefin interpolymers, wherein the α-olefin is at least one $C_3$-$C_{20}$ α-olefin (for example, propylene, 1-butene, 1-pentene, 4-methyl-1-pentene, 1-heptene, 1-hexene, and 1-octene) and preferably the at least one $C_3$-$C_{20}$ α-olefin is 1-butene, 1-hexene, 1-heptene or 1 octene. Most preferably, the ethylene/α-olefin interpolymer is a copolymer of ethylene and a $C_3$-$C_{20}$ α-olefin, and especially an ethylene/$C_4$-$C_8$ α-olefin copolymer such as an ethylene/1-octene copolymer, ethylene/1-butene copolymer, ethylene/1-pentene copolymer or ethylene/1-hexene copolymer. Suitable homogeneously branched linear ethylene polymers for use in the invention are sold under the designation of TAFMER by Mitsui Chemical Corporation and under the designations of EXACT and EXCEED resins by Exxon Chemical 5 Company.

The term "substantially linear ethylene polymer" as used herein means that the bulk ethylene polymer is substituted, on average, with 0.01 long chain branches/1000 total carbons to 3 long chain branches/1000 total carbons (wherein "total carbons" includes both backbone and branch carbons). Preferred polymers are substituted with 0.01 long chain branches/1000 total carbons to 1 long chain branches/1000 total carbons, more preferably from 0.05 long chain branches/1000 total carbons to 1 long chain branched/1000 total carbons, and especially from 0.3 long chain branches/1000 total carbons to 1 long chain branches/1000 total carbons.

As used herein, the term "backbone" refers to a discrete molecule, and the term "polymer" or "bulk polymer" refers, in the conventional sense, to the polymer as formed in a reactor. For the polymer to be a "substantially linear ethylene polymer", the polymer must have at least enough molecules with long chain branching such that the average long chain branching in the bulk polymer is at least an average of from 0.01/1000 total carbons to 3 long chain branches/1000 total carbons. The term "bulk polymer" as used herein means the polymer which results from the polymerization process as a mixture of polymer molecules and, for substantially linear ethylene polymers, includes molecules having an absence of long chain branching as well as molecules having long chain branching. Thus a "bulk polymer" includes all molecules formed during polymerization. It is understood that, for the substantially linear polymers, not all molecules have long chain branching, but a sufficient amount do such that the average long chain branching content of the bulk polymer positively affects the melt rheology (that is, the shear viscosity and melt fracture properties) as described herein below and elsewhere in the 5 literature.

Long chain branching (LCB) is defined herein as a chain length of at least one (1) carbon less than the number of carbons in the comonomer, whereas short chain branching (SCB) is defined herein as a chain length of the same number of carbons in the residue of the comonomer after it is incorporated into the polymer molecule backbone. For example, a substantially linear ethylene/1-octene polymer has backbones with long chain branches of at least seven (7) carbons in length, but it also has short chain branches of only six (6) carbons in length.

The substantially linear ethylene polymers used in the present invention are a unique class of compounds that are further defined in U.S. Pat. Nos. 5,272,236, 5,278,272 and 5,665,800. The substantially linear ethylene elastomers and plastomers for use in the present invention are further characterized as having:

(a) melt flow ratio, $I_{10}/I_2 \geq 5.63$, (b) a molecular weight distribution, Mw/Mn, as determined by gel permeation chromatography and defined by the equation: $(M_w/M_n) \leq (I_{10}/I_2) - 4.63$, (c) a gas extrusion rheology such that the critical shear rate at onset of surface melt fracture for the substantially linear ethylene polymer is at least 50 percent greater than the critical shear rate at the onset of surface melt fracture for a linear ethylene polymer, wherein the substantially linear ethylene polymer and the linear ethylene polymer comprise the same comonomer or comonomers, the linear ethylene polymer has an $I_2$ and Mw/Mn within ten percent of the substantially linear ethylene polymer and wherein the respective critical shear rates of the substantially linear ethylene polymer and the linear ethylene polymer are measured at the same melt temperature using a gas extrusion rheometer, (d) a single differential scanning calorimetry, DSC, melting peak between −30 and 150 C, and (e) a density less than or equal to 0.895 g/cm$^3$.

Determination of the critical shear rate and critical shear stress in regards to melt fracture as well as other rheology properties such as "rheological processing index" (PI), is performed using a gas extrusion rheometer (GER). The gas extrusion rheometer is described by M. Shida, R. N. Shroff and L. V. Cancio in Polymer Engineering Science, Vol. 17, No. 11, p. 770 (1977) and in Rheometers for Molten Plastics by John Dealy, published by Van Nostrand Reinhold Co. (1982) on pp. 97-99.

An apparent shear stress vs. apparent shear rate plot is used to identify the melt fracture phenomena over a range of nitrogen pressures from 5250 to 500 psig (369 to 35 kg/cm$^2$) using the die or GER test apparatus previously described.

The molecular weights and molecular weight distributions are determined by gel permeation chromatography (GPC). A suitable unit is a Waters 150 C high temperature chromatographic unit equipped with a differential refractometer and three columns of mixed porosity where columns are supplied by Polymer Laboratories and are commonly packed with pore sizes of $10^3$, $10^3$, $10^5$ and $10^6$ A. For ethylene polymers, the unit operating temperature is about 140° C. and the solvent is 1,2,4-trichlorobenzene, from which about 0.3 percent by weight solutions of the samples are prepared for injection. Conversely, for the substantially hydrogenated block polymers, the unit operating temperature is about 25° C. and tetrahydrofuran is used as the solvent. A suitable flow rate is about 1.0 milliliters/minute and the 5 injection size is typically about 100 microliters.

For the ethylene polymers where used in the present invention, the molecular weight determination with respect to the polymer backbone is deduced by using narrow molecular weight distribution polystyrene standards (from Polymer Laboratories) in conjunction with their elution volumes. The equivalent polyethylene molecular weights are determined by using appropriate Mark-Houwink coefficients for polyethylene and polystyrene (as described by Williams and Ward in Journal of Polymer Science, Polymer Letters, Vol. 6, p. 621, 1968) to derive the following equation:

$$M_{polyethylene} = a * (M_{polystyrene})b$$

In this equation, a=0.4316 and b=1.0. Weight average molecular weight, $M_w$, is calculated in the usual manner according to the following formula:

$$M_j = (\Gamma w_i(M_i^j))^j$$

where wi is the weight fraction of the molecules with molecular weight Mi eluting from the GPC column in fraction i, and j=1 when calculating $M_w$ and j=−1 when calculating $Mi_j$. For the at least one homogeneously branched ethylene polymer used in the present invention, the $M_w/M_n$ is preferably less than 3.5, more preferably less than 3.0, most preferably less than 2.5, and especially in the range of from 1.5 to 2.5 and most especially in the range from 1.8 to 2.3.

The homogeneously branched ethylene interpolymers (for example, substantially linear ethylene polymers and homogeneously branched linear ethylene polymers) used in the present invention are interpolymers of ethylene with at least one $C_3$-$C_{20}$ α-olefin and/or $C_4$-$C_{12}$ diolefin. Copolymers of ethylene and an Γ-olefin of $C_3$-$C_{20}$ carbon atoms are especially preferred. The term "interpolymer" as discussed above is used herein to indicate a copolymer, or a terpolymer, where, at least one other comonomer is polymerized with ethylene or propylene to make the interpolymer. Suitable unsaturated comonomers useful for polymerizing with ethylene include, for example, ethylenically unsaturated monomers, conjugated or non-conjugated dienes, polyenes, etc. Examples of such comonomers include $C_3$-$C_{20}$ α-olefins such as propylene, isobutylene, 1-butene, 1-hexene, 1-pentene, 4-methyl-1-pentene, 1-heptene, 1-octene, 1-nonene, and 1-decene. Preferred comonomers include propylene, 1-butene, 1-pentene, 1-hexene, 4-methyl-1-pentene, 1-heptene, and 1-octene, and 1-octene is especially preferred. Other suitable monomers include styrene, halo- or alkyl-substituted styrenes, vinylbenzocyclobutane, 1,4-hexadiene, 1,7-octadiene, and naphthenics (for example, cyclopentene, cyclohexene and cyclooctene).

In one preferred embodiment, at least one substantially hydrogenated block polymer is blended with at least one substantially linear ethylene polymer. In another preferred embodiment, at least one substantially hydrogenated block polymer is blended with at least one polypropylene polymer. Suitable polypropylene polymers for use in the invention, including random block propylene ethylene polymers, are available from a number of manufacturers, such as, for example, Montell Polyolefins and Exxon Chemical Company. From Exxon, suitable polypropylene polymers are supplied under the designations ESCORENE and ACHIEVE.

Other polymers that can be blended with either the substantially hydrogenated block polymer or the homogeneously branched ethylene interpolymer include, for example, but are not limited to, substantially hydrogenated block polymers, styrene block polymers, substantially linear ethylene polymers, homogeneously branched linear ethylene polymers, heterogeneously branched linear ethylene (including linear low density polyethylene (LLDPE), ultra or very low density polyethylene (ULDPE or VLDPE) medium density polyethylene (MDPE) and high density polyethylene (HDPE)), high pressure low density polyethylene (LDPE), ethylene/acrylic acid (EAA) copolymers, ethylene/methacrylic acid (EMAA) copolymers, ethylene/acrylic acid (EAA) ionomers, ethylene/methacrylic acid (EMAA) ionomers, ethylene/vinyl acetate (EVA) copolymers, ethylene/vinyl alcohol (EVOH) copolymers, polypropylene homopolymers and copolymers, ethylene/propylene polymers, ethylene/styrene interpolymers, graft-modified polymers (for example, maleic anhydride grafted polyethylene such as LLDPE g-MAH), ethylene acrylate copolymers (for example, ethylene/ethyl acrylate (EEA) copolymers, ethylene/methyl acrylate (EMA), and ethylene/methmethyl acrylate (EMMA) copolymers), polybutylene (PB), ethylene carbon monoxide interpolymer (for example, ethylene/carbon monoxide (ECO), copolymer, ethylene/acrylic acid/carbon monoxide (EAACO) terpolymer, ethylene/methacrylic acid/carbon monoxide (EMAACO) terpolymer, ethylene/vinyl acetate/carbon monoxide (EVACO) terpolymer and styrene/carbon monoxide (SCO)), chlorinated polyethylene and mixtures thereof.

The following examples are to illustrate the invention, and not to limit it. Ratios, parts and percentages are by weight unless otherwise stated.

EXPERIMENTAL

Fiber Descriptions:

Fiber made from Dow AFFINITY ethylene-octene copolymer (MI 3 g/10 min, density 0.875 g/cc) 140 Denier crosslinked by e-beam (19.2 mrad)

Generic spandex

Fabric Description:

3×1 RHT (right-hand twill); 100% cotton warp, 94% cotton/6% Crosslinked AFFINITY filling.

Example 1

Stone Washing

The stones were white pumas ranging approximately between 2-4 inches in diameter. The stones were soaked in the chemical solution for two (2) hours prior to testing.

Test Results:

To understand the effects of stone washing on spandex, a sample of stretch denim comprising spandex was run in parallel with a sample of stretch denim comprising AFFINITY fiber. Although the properties of the two fabrics cannot be compared directly (the fabrics are of slightly different constructions), the data does show, however, property degradation in spandex-based denims and property retention in AFFINITY-based denims.

| Test Procedures | AFFINITY Denim | | Spandex Denim | |
| --- | --- | --- | --- | --- |
| | Length | Width | Length | Width |
| Fabric Dimensional Change (AATCC 135) After Stone Wash, Chlorine Bleach | −2.2% | −1.6% | 4.9% | −10.2% |
| Fabric Dimensional Change (AATCC 135) After Stone Wash, Permanganate | −2.6% | −1.7% | −5.1% | −10.5% |
| Stretch and Recovery Comparison (ASTM D6614) | Stretch | Growth | Stretch | Growth |
| As Received | 7.0% | 2.9% | 17.3% | 4.5% |
| After 1x Stone Wash, Chlorine Bleach | 7.3% | 3.5% | 28.3% | 8.0% |
| After 1x Stone Wash, Permanganate | 7.5% | 3.5% | 29.9% | 10.1% |

| Stone Wash/Decolorize - Hypochlorite Formula | | | | | | |
| --- | --- | --- | --- | --- | --- | --- |
| Process | Liquor Ratio | Water Temp (F.) | Time (Min) | Chemical Quantity | Chemical | Comment |
| Stonewash/Hypochlorite | 10:1 | 140 | 90 | 10% soln. 5.25% available Cl (stone soak) | Sodium Hypochlorite | 3:1 Stone to Fabric ratio |
| Drain/Rinse | 10:1 | 170 | 10 | | | Rinse |
| Neutralize | 10:1 | 170 | 20 | 0.5 g/l | Sodium Disulfite | |
| Drain/rinse | | | | | | Rinse Hot Rinse Cold |
| Dry | | | | | | Tumble Dry Low |

| Stone Wash/Decolorize - Permanganate Formula | | | | | | |
| --- | --- | --- | --- | --- | --- | --- |
| Process | Liquor Ratio | Water Temp (F.) | Time (Min) | Chemical Quantity | Chemical | Comment |
| Stonewash/Potassium Permanganate | 10:1 | 140 | 90 | 5% soln. (stone soak) | Potassium Permanganate | 3:1 Stone to Fabric ratio |
| Drain/Rinse | 10:1 | 170 | 10 | | | Rinse |
| Neutralize | 10:1 | 170 | 20 | 0.5 g/l | Sodium Bisulfite | |
| Drain/rinse | | | | | | Rinse Hot Rinse Cold |
| Dry | | | | | | Tumble Dry Low |

Denim fabric containing AFFINITY fiber did not have any significant change in stretch properties. When a commercially available spandex containing stretch fabric was subjected to the hypochlorite and permangenate washes, it exhibited deterioration in stretch properties and dimensional stability.

Example 2

Stripping Agents

Chemical Reduction by 1 g/L Sodium Hydrosulfite (Dye Stripping), 100° C./212° F., 1 hour:

Dye Stripping is a process to chemically remove color from fabric for redying. This test was performed as sodium hydrosulfite is a commonly used dye stripping agent. Since published research has shown some sensitivity on the part of elastomeric fibers to dye-stripping. Dyers prefer to work with a fiber that can withstand a stripping bath rather than one that will not.

Fiber Description:

Fiber made from Dow AFFINITY EG 8200 (MI 5 g/10 min, density 0.870 g/cc) 70 Denier crosslinked by e-beam (32 mrad)

Dupont Lycra 70 Denier

Dupont Lycra—Chlorine Resistant 70 Denier

| Fiber Test Data | | | |
|---|---|---|---|
| | AFFINITY | Lycra | Lycra-CR |
| Ultimate Elongation After Treatment (%) | 276.68 | 334.94 | 297.26 |
| % Difference against as received | −16% | −23% | −28% |
| Breaking Load After Treatment (g) | 32.35 | 49.21 | 47.37 |
| % Difference against as received | −53 | −43 | −33 |

Example 3

Swimming Pool Water 100 ppm Sodium Hypochlorite (Chlorine Bleach), 50° C./120° F., 24 hours:

This accelerated test was performed as the hypochlorite ion is responsible both for bleaching and fiber damage in textiles, and it is also a chief cause in the degradation of fibers by swimming pool water. This level of chlorine was found by ruggedness testing to be roughly equivalent to the amount of exposure that would cause failure in a chlorine resistant Lycra® swimsuit after five months of use in which the suit was worn three times per week.

Fiber description:

P Fiber made from Dow AFFINITY EG 8200 (MI 5 g/10 min, density 0.870 g/cc) 70 Denier crosslinked by e-beam (32 mrad)

Dupont Lycra 70 Denier

Dupont Lycra—Chlorine Resistant 70 Denier

| | AFFINITY | Lycra | Lycra-CR |
|---|---|---|---|
| Ultimate Elongation After Treatment (%) | 250.23 | 125.83 | 206.50 |
| % Difference against as received | −24% | −71% | −50% |
| Breaking Load After Treatment (g) | 38.46 | 2.12 | 15.19 |
| % Difference against as received | −44% | −98% | −79% |

Example 4

Wear Test

Fiber description:

Fiber made from Dow AFFINITY EG 8200 (MI 5 g/10 min, density 0.870 g/cc) 70 Denier crosslinked by e-beam (32 mrad)

A Speedo suit made of a two bar tricot construction with nylon and conventional Lycra spandex was obtained that displayed almost complete disintegration of the spandex component. Additionally new Speedo suits containing chlorine resistant Lycra spandex were purchased, and a swimsuit was constructed using weft knit polyester (about 88% by weight)/Dow AFFINITY fiber (about 12% by weight) fabric.

Figure 2:
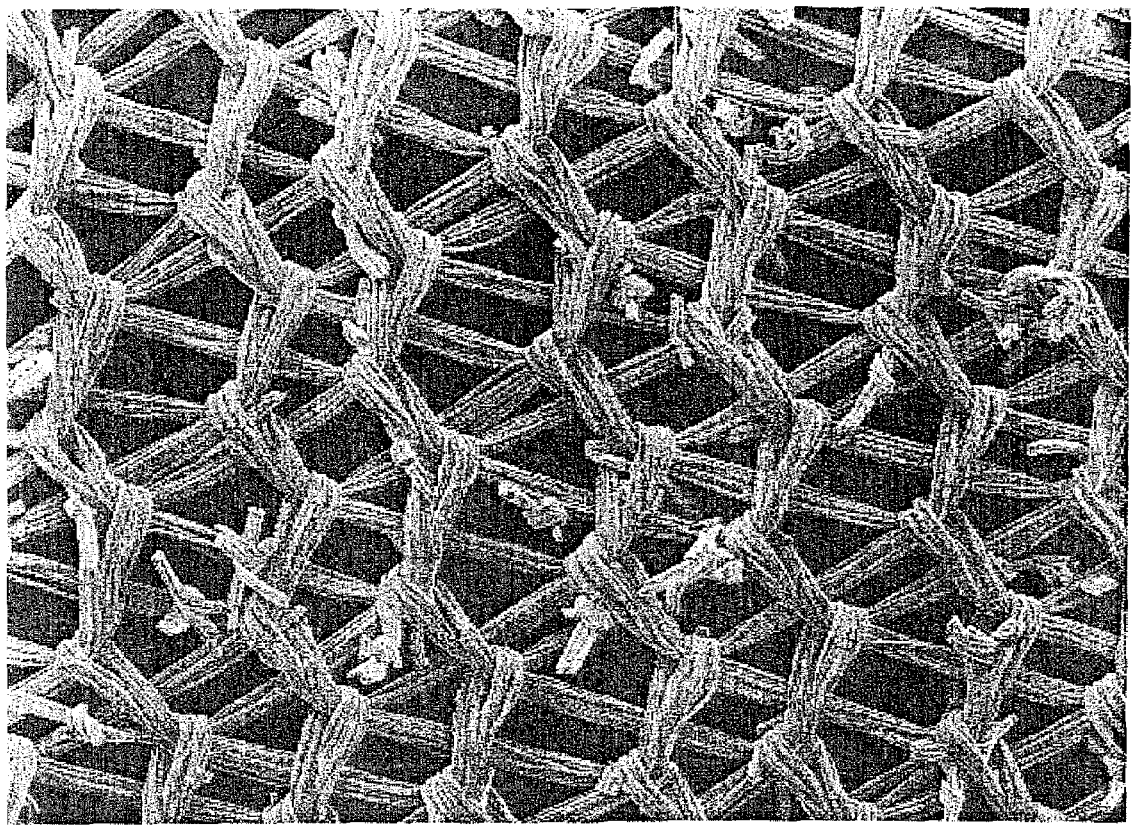
FIG. 2 is a Scanning Electron Microscopy (SEM) image of a Speedo swimsuit after a five-month wear test. The suit is of a tricot warp knit structure made with a chlorine-resistant Lycra™ fiber.
Figure 3:
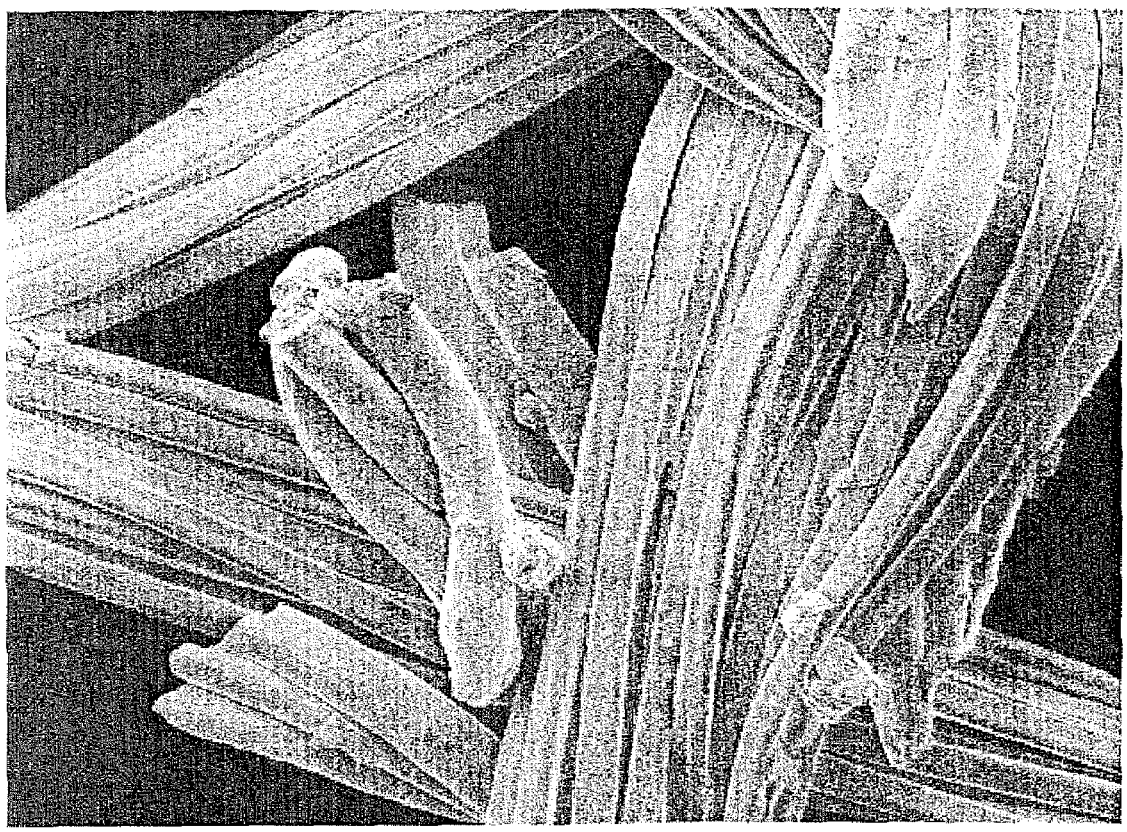
FIG. 3 is an SEM image of the swimsuit of FIG. 2 showing the loop structure under enhanced magnification.

After a five-month wear trial test, the chlorine resistant suit displayed localized degradation. Scanning Electron Microscopy (SEM) images (FIGS. 2 and 3) revealed that this degradation involved only the spandex filaments which were heavily degraded while the nylon filaments were untouched.

Figure 4:
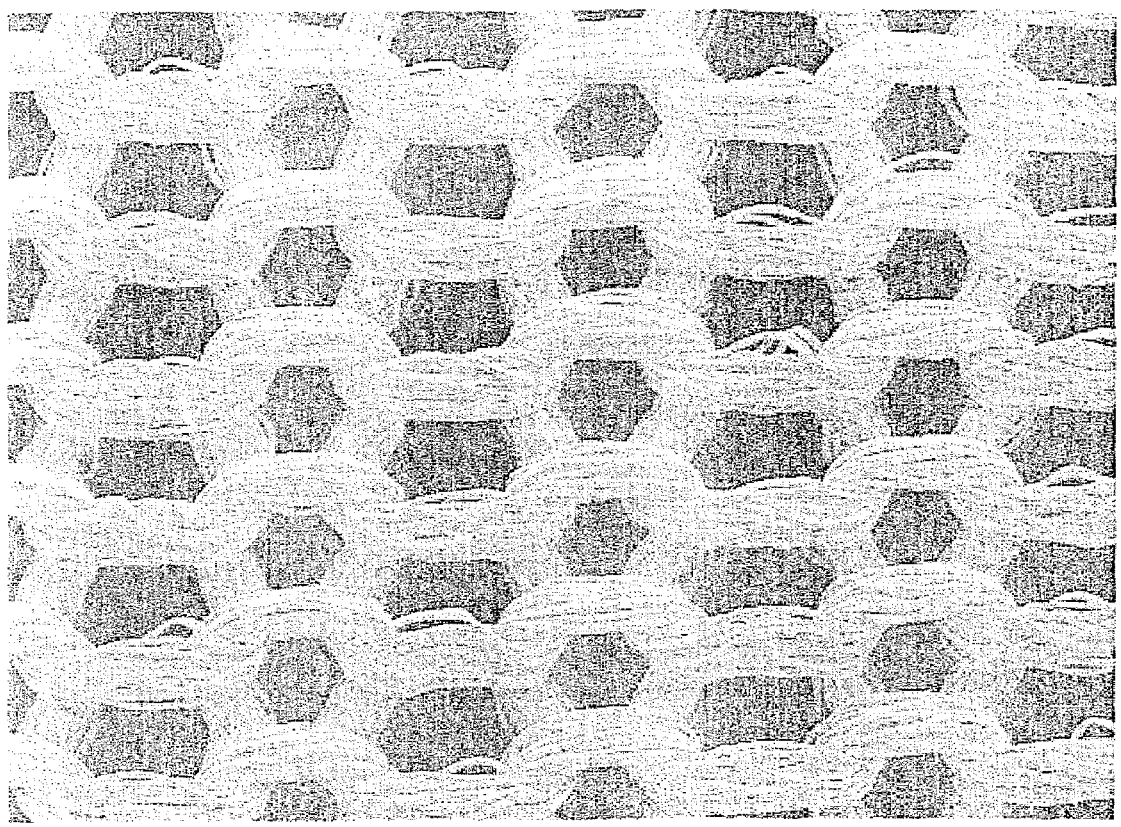
FIG. 4 is a SEM image of a Speedo swimsuit after a four-month wear test. The suit is of a weft knit single jersey structure made with a crosslinked AFFINITY ethylene/1-octene copolymer fiber.
Figure 5:
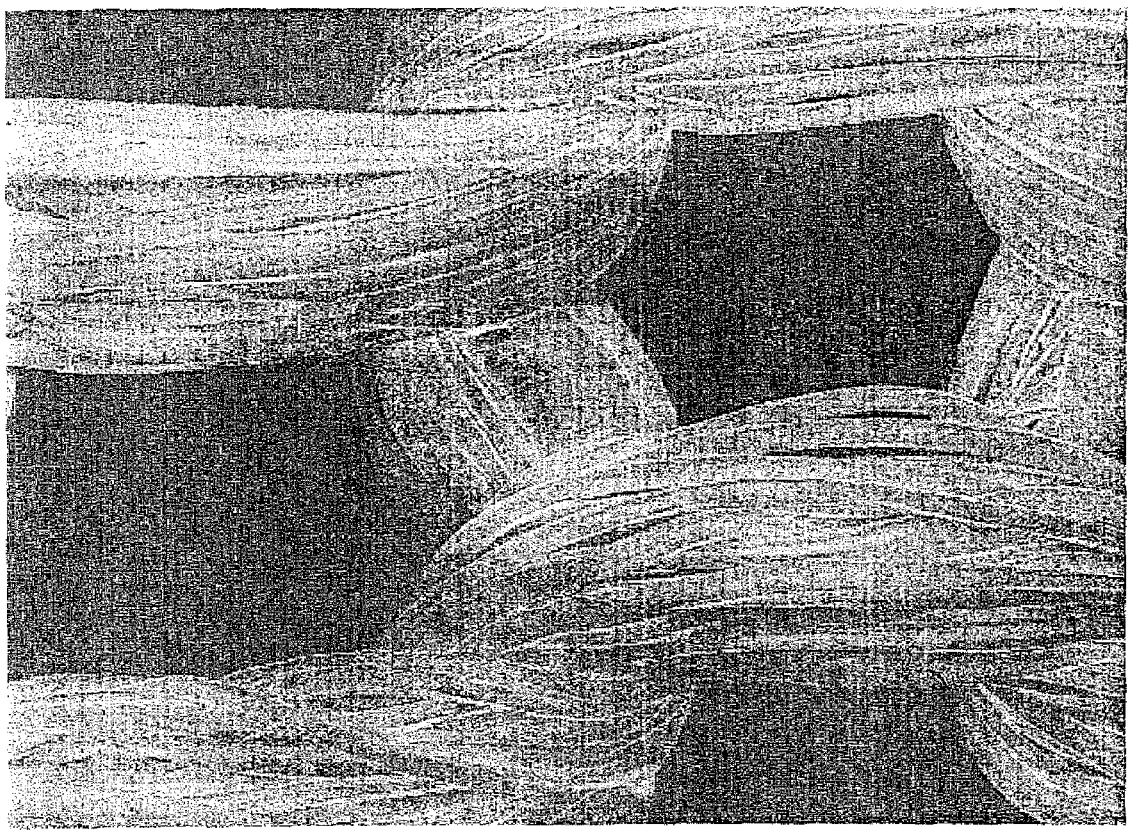
FIG. 5 is an SEM image of the swimsuit of FIG. 4 showing the loop structure under enhanced magnification.

In contrast to the chlorine resistant spandex, the crosslinked AFFINITY elastomeric yarn contained in a similar swimsuit used in a four month wear trial displayed no degradation (FIGS. 4 and 5). No significant bagging of the AFFINITY suit was found present and the suit was found to be functional in all ways with exception of the polyester yarn's propensity to stain readily when exposed to zinc oxide sun block, sun tan lotion and oil.

After completion of the wear trial, the AFFINITY suit was washed using the machine wash/warm tumble dry low cycle. The suit improved in appearance due to removal of stains and dirt accumulated over the period of the wear trial. After washing, the suit continued to fit well without bagging or excess shrinkage.

Example 5

Laundering

Stretch Properties of Fabric Containing AFFINITY Crosslinked Fibers:

Fabric description: 3×1 LHT (left-hand twill); 100% Nylon T-66 warp, 84% cotton/16% Dow AFFINITY EG 8200 (MI 5 g/10 min, density 0.870 g/cc) 70 Denier crosslinked by e-beam (22.4 mrad) filling.

| Laundry Method | Conditions | Fabric Stretch, % weft direction (ASTM-D-6614-00) | | |
|---|---|---|---|---|
| | | 1 cycle | 25 cycles | 50 cycles |
| MWH TDH SIM | From AATCC Test Method 135 machine wash hot (normal cycle, 12 minutes), 140° F. tumble dry high, 160° F. steam iron medium, 300° F. | 66.6 | 70.2 | 73.0 |
| MWH TDH SIM With Chlorine (CLOROX ®) | From AATCC Test Method 135 machine wash hot (normal cycle, 12 minutes), 140° F. tumble dry high, 160° F. steam iron medium, 300° F. | 65.0 | 70.1 | 74.6 |
| MWH TDH SIM With Non-Chlorine Bleach (CLOROX 2 ®) | From AATCC Test Method 135 machine wash hot (normal cycle, 12 minutes), 140° F. tumble dry high, 160° F. steam iron medium, 300° F. | 64.1 | 66.4 | 71.0 |

The data in the above table demonstrates that the fabric experiences minimal change over 1 to 50 cycles.

Although the invention has been described in considerable detail through the preceding embodiments, this detail is for the purpose of illustration. Many variations and modifications can be made on this invention without departing from the spirit and scope of the invention as described in the following claims. All U.S. patents and allowed U.S. patent applications cited above are incorporated herein by reference.

What is claimed is:

1. A process for preparing a treated woven or knitted durable elastic article comprising the steps of:
   a) selecting an article which comprises a yarn comprising a monofilament elastic fiber that will recover at least about 50% of its stretched length after the first pull and after the fourth pull to 100% strain and an inelastic fiber;
   b) exposing said article to a treatment wherein said treatment is selected from the group consisting of:
      i) exposure to a 10% by weight sodium hypochlorite solution for a period of at least 90 minutes at a temperature of at least 140° F.; and
      ii) exposure to a 5% by weight permanganate solution for a period of at least 90 minutes at a temperature of at least 140° F.;
   wherein after step (b), such article exhibits growth of less than 20% as determined according to ASTM D3107, wherein the monofilament elastic fiber comprises crosslinked homogeneously branched ethylene polymer.

2. The process of claim 1 wherein the growth is less than 10%.

3. The process of claim 1 wherein the growth is less than 8%.

4. The process of claim 3 which has been subjected to two or more of the treatments.

5. The process of claim 3 wherein the article is stone washed.

6. The process of claim 1 wherein the article is a fabric.

7. The process of claim 6 wherein the fabric is denim.

8. The process of claim 1 wherein the article is a garment.

9. The process of claim 8 wherein the garment is swimwear.

10. The process of claim 9 wherein the garment is a uniform.

11. The process of claim 10 wherein the uniform is a rental uniform.

12. The process of claim 1, wherein the monofilament elastic fiber has been subjected to at least 19.2 mrad of ionizing radiation.

* * * * *